United States Patent
Raths et al.

(10) Patent No.: US 6,828,452 B2
(45) Date of Patent: Dec. 7, 2004

(54) METHOD FOR PRODUCING ACYL AMINO ACIDS

(75) Inventors: Hans-Christian Raths, Monheim (DE); Andreas Syldath, Monheim (DE); Karl Heinz Schmid, Mettmann (DE); Juergen Falkowski, Monheim (DE); Ingomar Mrozek, Duesseldorf (DE); Josef Koester, Duesseldorf (DE)

(73) Assignee: Cognis Deutschland GmbH & Co. KG, Duesseldorf (DE)

(*) Notice: Subject to any disclaimer, the term of this patent is extended or adjusted under 35 U.S.C. 154(b) by 0 days.

(21) Appl. No.: 10/466,402
(22) PCT Filed: Jan. 9, 2002
(86) PCT No.: PCT/EP02/00123
§ 371 (c)(1), (2), (4) Date: Jul. 15, 2003
(87) PCT Pub. No.: WO02/057217
PCT Pub. Date: Jul. 25, 2002

(65) Prior Publication Data
US 2004/0063980 A1 Apr. 1, 2004

(30) Foreign Application Priority Data
Jan. 18, 2001 (DE) .......................... 101 02 008
Aug. 31, 2001 (DE) .......................... 101 42 469

(51) Int. Cl.⁷ ............................................. C07C 231/00
(52) U.S. Cl. ............................................. 554/69; 554/68
(58) Field of Search .................................. 554/68, 69

(56) References Cited

U.S. PATENT DOCUMENTS

| 4,172,887 A | 10/1979 | Vanlerberghe et al. |
| 5,705,169 A | 1/1998 | Stein et al. |
| 5,730,960 A | 3/1998 | Stein et al. |
| 5,942,635 A | 8/1999 | Ehle et al. |
| 5,945,091 A | 8/1999 | Habeck et al. |
| 6,193,960 B1 | 2/2001 | Metzger et al. |

FOREIGN PATENT DOCUMENTS

| DE | 1 165 574 A | 3/1964 |
| DE | 2 024 051 A | 12/1971 |
| DE | 197 12 033 A1 | 9/1998 |
| DE | 197 56 377 A1 | 6/1999 |
| EP | 0 693 471 B1 | 1/1996 |
| EP | 0 694 521 B1 | 1/1996 |
| EP | 0 781 835 B1 | 7/1997 |
| EP | 0 818 450 B1 | 1/1998 |
| EP | 0 827 950 B1 | 3/1998 |
| EP | 0 857 717 B1 | 8/1998 |
| FR | 2 252 840 A | 8/1975 |

(List continued on next page.)

OTHER PUBLICATIONS

Falbe, "Surfactants in Consumer Products", Springer Verlag, Berlin, (1987), pp. 54–124.

(List continued on next page.)

Primary Examiner—Deborah D. Carr
(74) Attorney, Agent, or Firm—Aaron R. Ettelman

(57) ABSTRACT

Acylamino acids are made by a process which comprises the steps of: (1) introducing a mixture comprised of at least one amino acid or amino acid salt and an alkali source into a reaction zone; (2) adding a mixture comprised of a fatty acid halide of the formula (I):

$$R^1COX \qquad (I)$$

wherein $R^1$ is an alkyl or alkenyl group having from 6 to 22 carbon atoms and X is chlorine, bromine or iodine to form a reaction mixture while continuously circulating the reaction mixture from the reaction zone through a mixing zone until all of the second mixture has been added to the reaction zone. The process guarantees uniform mixing of the reaction components without the foaming observed without the use of a mixing zone.

7 Claims, 2 Drawing Sheets

A Plant concept for Examples 1 to 5:

FOREIGN PATENT DOCUMENTS

| | | |
|---|---|---|
| FR | 2 760 746 A1 | 9/1998 |
| GB | 962919 A | 7/1964 |
| GB | 1 333 475 A | 10/1973 |
| WO | WO 97/00434 A1 | 1/1997 |
| WO | WO 97/16409 A1 | 5/1997 |
| WO | WO 00/40546 A1 | 7/2000 |

OTHER PUBLICATIONS

Falbe, "Katalysatoren, Tenside und Mineralöladditive" (Catalysts, Surfactants and Mineral Oil Additives), Thieme Verlag, Stuttgart, (1978), pp. 123–217.

Lochhead et al., "Encyclopedia of Polymers and Thickeners for Cosmetics", Cosmetics & Toiletries, vol. 108, (May, 1993), pp. 95–114, 116–124, 127–130, 132–135.

Todd et al., "Volatile silicone fluids for cosmetic formulations", Cosmetics and Toiletries, vol. 91, (Jan., 1976), pp. 29–32.

Finkel, "Formulierung kosmetischer Sonnenschutzmittel", SÖFW–Journal, 122, (1996), pp. 543–546 & 548.

Finkel, "Formulierung kosmetischer Sonnenschutzmittel", Parfumerie und Kosmetik, 80, No. 3 (1999), pp. 10–12, 14–16.

"Kosmetische Färbemittel", Farbstoffkommission der Deutschen Forschungsgemeinschaft, Verlag Chemie, Weinheim, (1984), pp. 81–106.

A  Plant concept for Examples 1 to 5:

B  Plant concept for Comparison Example 1:

METHOD FOR PRODUCING ACYL AMINO ACIDS

BACKGROUND OF THE INVENTION

This invention relates to a process for the production of acylamino acids in which the fatty acid halide is introduced into a circulation pipe provided with a mixer while the mixture of an amino acid and an alkali source is accommodated in the reactor, to the product obtained and to the use of these acylamino acids in surfactant-containing preparations.

N-acylamino acids, such as N-acyl glutamates for example, are known from the prior art as mild co-surfactants for use in cosmetic preparations. They are prepared by reaction of fatty acid chlorides with the amino group of glutamic acid sodium salt in the presence of bases, such as NaOH for example, in aqueous medium. The disadvantage of this process is that the lipophilic fatty acid chloride is difficult to react with the hydrophilic amino acid or the basic salt in aqueous medium. Attempts have been made to eliminate this problem by adding organic solvents such as, for example, acetone, methylethyl ketone, dioxane, polyols, tetrahydrofuran, t-butanol or cyclohexane.

Acylation in the absence of solvents, but using intensive stirring energy, is known from European patent EP 0827950 A1. The disadvantage of this process is the vigorous foaming by which it is accompanied so that the process is unsuitable for industrial application. This foaming can additionally lead to mixing problems where acid chloride or alkali is introduced. Accordingly, this process is not suitable for the production of acylamino acids on an industrial scale.

Patent application EP 0857717 A1 describes a process for the production of acylamino acids by reaction with fatty acid halides in the presence of water, alkali and polyols in conventional stirred tank reactors on the lines of a one-pot reaction. The disadvantages of this process lie in the sometimes very large quantities of polyol that are needed for an adequate yield and in the unsatisfactory mixing. The large polyol contents mentioned in the document in question are sometimes undesirable for the use of the resulting acylated amino acids. However, any reduction in the polyol content impacts adversely on the low-temperature behavior of the product.

Accordingly, the problem addressed by the invention was to provide a process for the production of acylamino acids which would guarantee uniform mixing of the reaction components without the foaming observed in traditional stirred reactors, and a product which would be distinguished by high stability at low temperatures and in storage.

DESCRIPTION OF THE INVENTION

Figure 1:
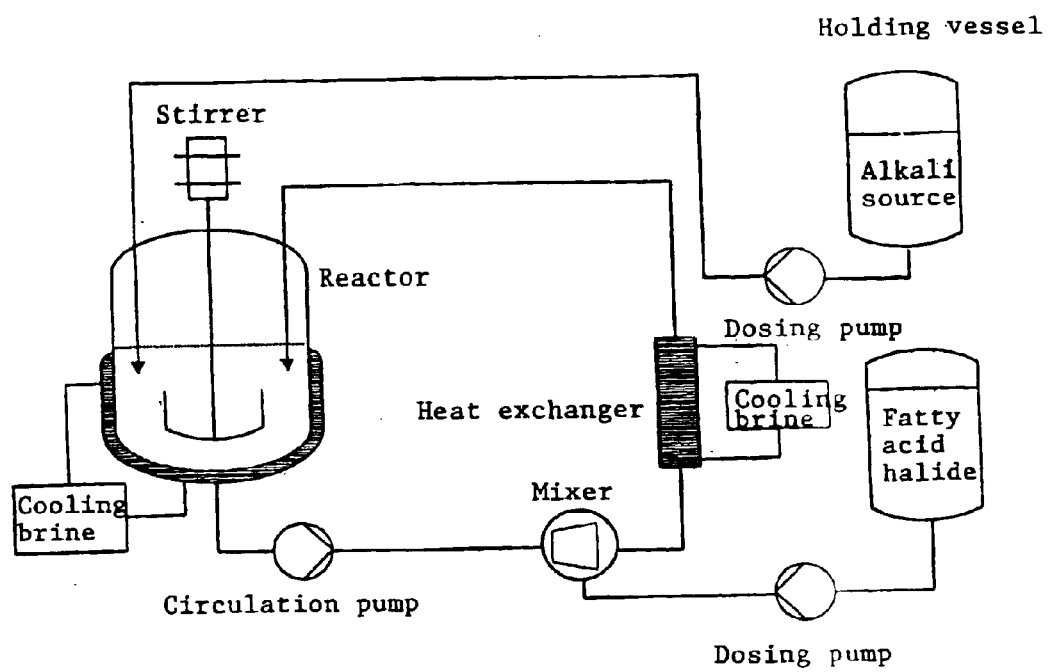
FIG. 1 is a process flow for a process for the production of acylamino acids which includes a mixer.

The present invention relates to a process for the production of acylamino acids in which a mixture of at least one amino acid or amino acid salt and an alkali source is placed in a reactor and fatty acid halides corresponding to formula (I):

$$R^1COX \qquad (I)$$

in which $R^1$ is an alkyl or alkenyl group containing 6 to 22 carbon atoms and X is chlorine, bromine or iodine, are added to the mixture in a mixing element.

It has surprisingly been found that acylamino acids can be produced without the excessive foaming observed in traditional stirred reactors, so that uniform mixing of the reaction components, i.e. the amino acids, the alkali source and the fatty acid halides, is guaranteed.

The present invention also relates to an acylamino acid mixture containing (a) 3 to 10% by weight of sodium chloride,
(b) 0.1 to 4% by weight of free fatty acids,
(c) 1 to 11% by weight of free amino acids,
(d) 0.1 to 6% by weight of low molecular weight alcohol and
(e) 30 to 80% by weight of water.

This product is obtainable by not removing the water-soluble and/or water-dispersible organic solvents added after the process according to the invention has been carried out. The acylamino acid product thus has a content of water-soluble and/or water-dispersible solvents, preferably low molecular weight monoalcohols, of 0.1 to 6%, preferably 0.2 to 3% and more particularly in the range from 0.5 to 2.0%, based on the water-containing surfactant paste which, for its part, has a water content of 30 to 80% by weight, preferably 45 to 70% by weight and more particularly 50 to 65% by weight. The content of solvents subsequently added to ensure resistance to low temperatures can thus be significantly reduced. For example, only at most 6% by weight, preferably at most 4% by weight and more particularly 3% by weight of polyols need subsequently be added to achieve good low-temperature behavior. In favorable cases, there is no need at all for subsequently added solvents.

Amino Acids or Salts Thereof

According to the invention, suitable amino acids or amino acid salts are any α-amino acids known to the expert from the literature which can be acylated with fatty acid halides to form N-acylamino acids. Preferred amino acids are glutamic acid, sarcosine, aspartic acid, alanine, valine, leucine, isoleucine, proline, hydroxyproline, glycine, serine, cysteine, cystine, threonine, histidine and salts thereof and, more particularly, glutamic acid, sarcosine, aspartic acid, glycine, lysine and salts thereof. Glutamic acid, sarcosine, aspartic acid, glycine and lysine are particularly preferred. The amino acids may be used in optically pure form or as racemic mixtures.

The amino acids or their salts are used in quantities of 20 to 70, preferably 35 to 60 and more particularly 40 to 50% by weight, based on the starting mixture, i.e. before addition of the acid chloride, in the production of the surfactant mixtures in accordance with the invention.

Fatty Acid Halides

Fatty acid halides—component (b)—corresponding to formula (I):

$$R^1COX \qquad (I)$$

in which $R^1$ is an alkyl or alkenyl group containing 6 to 22, preferably 8 to 18 and more particularly 8 to 16 carbon atoms and X represents chlorine, bromine or iodine, preferably chlorine, are used for the process according to the invention. Typical acid halides are octanoyl chloride, nonanoyl chloride, decanoyl chloride, undecanoyl chloride, lauroyl chloride, tridecanoyl chloride, myristyl chloride, palmitoyl chloride, stearoyl chloride, oleoyl chloride and mixtures thereof. The fatty acid halides are used in a molar ratio of acylatable compound to acid halide of 1 to 1.5 and preferably 1.15 to 1.3 in the production of the surfactant mixtures in accordance with the invention.

Alkali Source

For the process according to the invention, an alkali source is placed in the reactor. In the context of the invention, the alkali source is understood to be alkali metal hydroxide or carbonate dissolved in water or in a mixture of water and/or at least one water-soluble organic solvent. An aqueous solution of alkali metal hydroxide or alkali metal hydroxide, more particularly sodium hydroxide, dissolved in water or water-soluble organic solvents is preferably used (cf. process).

In the process according to the invention, the quantity of alkali is gauged so that the starting mixture of amino acid or amino acid salt is adjusted to a pH of 10 to 12.5 and preferably in the range from 11.5 to 12.5.

Water-soluble Organic Solvents

Suitable water-soluble or water-dispersible organic solvents are, for example, acetone, methylethyl ketone, dioxane, tetrahydrofuran, methanol, ethanol, propanol, i-propanol, butanol, t-butanol, pentanol, isopentanol, trimethyl hexanol, glycerol, ethylene glycol, 2-methylpropane-1,3-diol, propylene glycol, dipropylene glycol, 1,3-butylene glycol, butane-1,2-diol, butane-1,4-diol, isopentyl diol, sorbitol, xylitol, mannitol, erythritol, pentaerythritol, ethanolamine, triethanolamine, 2-amino-2-methylpropanol, 1-amino-2-propanol, 1-amino-2-butanol, 1-methoxy-2-propanol, 2-methoxy ethanol, 2-ethoxy ethanol, 2-propoxy ethanol, 2-isopropoxy ethanol, 2-butoxy ethanol, 1-methoxy-2-propanol, 1-ethoxy-2-propanol, 1-propoxy-2-propanol, 1-isopropoxy-2-propanol, 1-butoxy-2-propanol, 1-isobutoxy-2-propanol, methoxy isopropanol, diethylene glycol monomethyl ether, diethylene glycol monoethyl ether, diethylene glycol monopropyl ether, diethylene glycol monoisopropyl ether, diethylene glycol monobutyl ether, triethylene glycol monomethyl ether, triethylene glycol monoethyl ether, triethylene glycol monopropyl ether, triethylene glycol monoisopropyl ether, triethylene glycol monobutyl ether, dipropylene glycol monomethyl ether, dipropylene glycol monoethyl ether, dipropylene glycol monopropyl ether, dipropylene glycol monoisopropyl ether, dipropylene glycol monobutyl ether, hexylene glycol, triacetin, propylene carbonate, glycerol carbonate. Preferred solvents are ethanol, isopropanol, diethylene glycol monoethyl ether and triethanolamine. These solvents are also placed in the reactor together with the amino acid and the alkali source.

The water-soluble organic solvents are used in quantities of 0.1 to 15, preferably 0.2 to 7 and more particularly 0.2 to 4.0% by weight in the process according to the invention.

Process

A mixture of at least one amino acid or amino acid salt, preferably an aqueous solution of an amino acid or amino acid salt, and an alkali source, preferably alkali metal hydroxide or alkali metal carbonate dissolved in water and/or aqueous organic solvents, is introduced into a reactor (FIG. 1) and cooled to 10–20° C. In one particular embodiment of the invention, water-soluble organic, preferably readily volatile solvents may also be added, as described above. The reactor and the circulation system are provided with a cooling jacket which dissipates the heat of reaction and guarantees a maximum temperature of 20–25° C. Before the start of the reaction, the pH is adjusted to ca. 12 with alkali metal solution, preferably sodium hydroxide. The fatty acid halide and the alkali metal solution are then simultaneously added (see plant concept) at such a rate that the reactor temperature does not exceed 20–25° C. and the pH stays between 11.5 and 12.5. Of the two reactants, the alkali source is preferably added to the reactor beneath the surface of the reaction mixture while the fatty acid chloride is added from the holding vessel either to or before the mixing element (mixer). In the context of the invention, a mixing element is understood to be a dynamic or static mixer. Mixers are understood to be encapsulated units which prevent air from entering during the mixing process. They may be dynamic mixers with moving and, optionally, fixed internals or static mixers with only static internals (mixing using the flow energy). The reactor and the mixing element are connected by a circulation system. A circulation pump circulates the reaction mixture throughout the reaction, the mixture being returned to the reactor beneath the surface of the reaction mixture. After addition of the fatty acid chloride, the reaction mixture is stirred for another 2 to 5 hours and preferably for another 2 hours at 20–25° C. and is then heated for another 2 to 5 hours and preferably for 2 hours to 60–80° C. If organic solvents have been added as additional components, they may be removed from the reaction mixture by distillation, preferably vacuum distillation or steam distillation.

Since these solvents generally distil over as an azeotrope with water, the resulting increase in concentration is reversed by addition of an adequate quantity of water. This distillation is preferably carried out while steam is introduced which, on the one hand, reduces foaming during the distillation step and, on the other hand, replaces the lost water. The distillation step is preferably carried out at 60 to 80° C. under a pressure of 200 to 400 mbar.

In one particular embodiment of the invention, the organic solvents are largely removed from the mixture by distillation when the reaction is over and any small quantities of solvent still present are removed by means of a so-called Fryma unit. In another embodiment of the invention, the solvent can also be removed from the mixture by a membrane process. However, the solvent is preferably not removed, particularly where low molecular weight monoalcohols are used.

The reaction mixture is then left to cool to room temperature and adjusted to a pH of ca. 10 by addition of dilute hydrochloric acid. The reaction solution contains ca. 20 to 45% by weight and preferably 25 to 30% by weight acylated amino acid. In order to minimize foaming, the reaction mixture is stirred at a speed of less than 60 r.p.m. and preferably less than 30 r.p.m. in the reactor. Mixing in the absence of air avoids foaming throughout the entire process.

Commercial Applications

The acylamino acid mixtures produced by the process according to the invention contain 3 to 10% by weight sodium chloride, 0.1 to 4% by weight free fatty acids, 1 to 11% by weight free amino acids, 0.1 to 6% by weight low molecular weight alcohol and 30 to 80% by weight water.

Preferred acylamino acid mixtures contain 4 to 7% by weight sodium chloride, 0.5 to 3% by weight free fatty acids, 1.5 to 8% by weight free amino acids, 0.2 to 3% by weight low molecular weight alcohol and 45 to 70% by weight water.

Particularly preferred acylamino acid mixtures contain 4 to 5.5% by weight sodium chloride, 1 to 2.5% by weight free fatty acids, 3 to 6% by weight free amino acids, 0.5 to 2% by weight low molecular weight alcohol and 50 to 65% by weight water.

Where isopropanol and/or ethanol is/are used as the low molecular weight alcohol, at most 6% by weight, preferably at most 4% by weight and more particularly at most 3% by weight 1,2-propylene glycol is added to that product.

The product may be used in surface-active preparations such as, for example, laundry and dishwashing detergents, household cleaners and cosmetic and/or pharmaceutical preparations in quantities of 0.1 to 30% by weight, preferably 0.5 to 10% by weight and more particularly 1 to 5% by weight. These preparations may contain mild surfactants, oil components, emulsifiers, pearlizing waxes, consistency factors, thickeners, superfatting agents, stabilizers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosine inhibitors (depigmenting agents), hydrotropes, solubilizers, preservatives, perfume oils, dyes and the like as further auxiliaries and additives. Cosmetic and/or pharmaceutical cleaning preparations include, for example, hair shampoos, oral hygiene and dental care preparations, hair lotions, foam baths, shower baths, creams, gels, lotions, alcoholic and aqueous/alcoholic solutions and emulsions.

Surfactants

Suitable surfactants are anionic, nonionic, cationic and/or amphoteric surfactants which may be present in the preparations in quantities of normally about 1 to 70% by weight, preferably 5 to 50% by weight and more preferably 10 to 30% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl(ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol ethers, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols (cf. DE 19756377 A1), more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids (cf. EP 97/00434), esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates such as, for example, Dicaprylyl Carbonate (Cetiol® CC), Guerbet carbonates based on $C_{6-18}$ and preferably $C_{8-10}$ fatty alcohols, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols, silicone oils (cyclomethicone, silicon methicone types, etc.) and/or aliphatic or naphthenic hydrocarbons, for example squalane, squalene or dialkyl cyclohexanes.

Emulsifiers

Suitable emulsifiers are, for example, nonionic surfactants from at least one of the following groups:

products of the addition of 2 to 30 mol ethylene oxide and/or 0 to 5 mol propylene oxide onto linear $C_{8-22}$ fatty alcohols, onto $C_{12-22}$ fatty acids, onto alkyl phenols containing 8 to 15 carbon atoms in the alkyl group and alkylamines containing 8 to 22 carbon atoms in the alkyl group;

alkyl and/or alkenyl oligoglycosides containing 8 to 22 carbon atoms in the alk(en)yl group and ethoxylated analogs thereof;

addition products of 1 to 30 mol ethylene oxide onto fatty acids;

insertion products of 1 to 30 mol ethylene oxide into fatty acid methyl esters;

addition products of 1 to 15 mol ethylene oxide onto castor oil and/or hydrogenated castor oil;

addition products of 15 to 60 mol ethylene oxide onto castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and adducts thereof with 1 to 30 mol ethylene oxide;

partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and adducts thereof with 1 to 30 mol ethylene oxide;

mixed esters of pentaerythritol, fatty acids, citric acid and fatty alcohol according to DE 11 65 574 PS and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, block copolymers, for example Polyethyleneglycol-30 Dipolyhydroxystearate;

polymer emulsifiers, for example Pemulen types (TR-1, TR-2) of Goodrich;

polyalkylene glycols and glycerol carbonates.

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as lipid layer enhancers for cosmetic formulations from DE 20 24 051 PS.

Alkyl and/or alkenyl oligoglycosides, their production and their use are known from the prior art. They are produced in particular by reacting glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide with the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Typical examples of suitable polyglycerol esters are Polyglyceryl-2 Dipolyhydroxystearate (Dehymuls® PGPH), Polyglycerol-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Poly-glyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 mol ethylene oxide.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of *Cocamidopropyl Betaine* is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Finally, cationic surfactants are also suitable emulsifiers, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs) correspond to the following general formula:

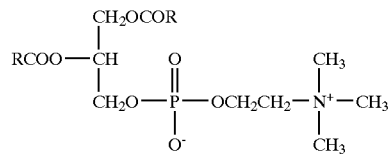

where R typically represents linear aliphatic hydrocarbon radicals containing 15 to 17 carbon atoms and up to 4 cis-double bonds. Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycero-phosphates) which are normally classed as fats. Sphingosines and sphingolipids are also suitable.

Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat550, Chemviron), polyaminopolyamides as described, for example, in FR 2252840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/ acrylate copolymers, octylacrylamide/methyl methacrylate/ tert.-butylaminoethyl methacrylate/2-hydroxypropyl methacrylate copolymers, polyvinyl pyrrolidone, vinyl pyrrolidone/vinyl acetate copolymers, vinyl pyrrolidone/ dimethylaminoethyl methacrylate/vinyl caprolactam terpolymers and optionally derivatized cellulose ethers and silicones. Other suitable polymers and thickeners can be found in Cosm. Toil. 108, 95 (1993).

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives as described in EP 0694521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione and the enamine compounds described in DE 197 12 033 A1 (BASF). The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble lightblocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments are preferably used in sun protection products. Micronized zinc oxide is preferably used. Other suitable UV filters can be found in P. Finkel's review in SÖFW-Journal 122, 543 (1996) and in Parf. Kosm. 3, 11 (1999).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Biogenic Agents

Biogenic agents in the context of the invention are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers. Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of labdanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants reduce perspiration and thus counteract underarm wetness and body odor by influencing the activity of the eccrine sweat glands. Aqueous or water-free antiperspirant formulations typically contain the following ingredients:

astringent active principles, oil components, nonionic emulsifiers, co-emulsifiers, consistency factors, auxiliaries in the form of, for example, thickeners or complexing agents and/or non-aqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example, inflammation-inhibiting, skin-protecting or pleasant-smelling essential oils, synthetic skin-protecting agents and/or oil-soluble perfume oils.

Typical water-soluble additives are, for example, preservatives, water-soluble perfumes, pH regulators, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Swelling Agents

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Insect Repellents

Suitable insect repellents are N,N-diethyl-m-toluamide, pentane-1,2-diol or Ethyl Butylacetylaminopropionate.

Self-tanning Agents and Depigmenting Agents

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils

Suitable perfume oils are mixtures of natural and synthetic fragrances. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemi, W inheim, 1984, pages 81 to 106. These dyes are normally used in concentrations of 0.001 to 0.1% by weight, based on the mixture was a whole.

The total percentage content of auxiliaries and additives may be from 1 to 80% by weight and is preferably from 5 to 50% by weight and more particularly from 7 to 10% by weight, based on the particular preparation. The preparations may be produced by standard cold or hot emulsification processes or by the phase inversion temperature (PIT) method.

EXAMPLES

I. Production of Acylamino Acids

Example 1

Production of $C_{12}$–$C_{18}$ Acyl Glutamate Disodium Salt Without Removal of the Solvent 1,300 kg water, 10 kmol=1,870 kg monosodium glutamate (×1 $H_2O$), 100 kg isopropyl alcohol and 1,100 kg 33% sodium hydroxide are introduced into a 15 $m^3$ reactor (FIG. 1) and stirred until a clear solution is obtained. The solution obtained is cooled to 10–20° C. The reactor and the circulation system are provided with a cooling jacket which dissipates the heat of reaction and guarantees a maximum temperature of 20–25° C. Before the start of the reaction, the pH is adjusted to ca. 12 with 11% sodium hydroxide. 7.7 kmol=1,825 kg cocoyl fatty acid chloride and 4,500 kg 11% NaOH are then simultaneously added (see plant concept) at such a rate that the reactor temperature does not exceed 20–25° C. and the pH stays between 11.5 and 12.5. Of the two reactants, the sodium hydroxide is preferably added to the reactor beneath the surface of the reaction mixture while the acid chloride is added from the holding vessel either to or before the mixer. A circulation pump circulates the reaction mixture throughout the reaction, the mixture being returned to the reactor beneath the surface of the reaction mixture. After addition of the fatty acid chloride, the reaction mixture is stirred for another 2 hours at 20–25° C. in the reactor and is then heated for about another 2 hours to 60–80° C. The reaction mixture is then left to cool to room temperature and adjusted to a pH of ca. 10 by addition of dilute hydrochloric acid.

The content of $C_{12}$–$C_{18}$ acyl glutamate disodium salt in the end product is 26%.

Example 2

Production of $C_{12}$–$C_{18}$ Acyl Glutamate Disodium Salt Without Removal of the Solvent 1,300 kg water, 10 kmol=1,870 kg monosodium glutamate (×1 $H_2O$), 135 kg ethanol and 1,100 kg 33% sodium hydroxide are introduced into a 15 $m^3$ reactor (FIG. 1) and stirred until a clear solution is obtained. The solution obtained is cooled to 10–20° C. The reactor and the circulation system are provided with a cooling jacket which dissipates the heat of reaction and guarantees a maximum temperature of 20–25° C. Before the start of the reaction, the pH is adjusted to ca. 12 with 11% sodium hydroxide. 7.7 kmol=1,825 kg cocoyl fatty acid chloride and 4,500 kg 11% NaOH are then simultaneously added (see plant concept) at such a rate that the reactor temperature does not exceed 20–25° C. and the pH stays between 11.5 and 12.5. Of the two reactants, the sodium hydroxide is preferably added to the reactor beneath the surface of the reaction mixture while the acid chloride is added from the holding vessel either to or before the mixer. A circulation pump circulates the reaction mixture throughout the reaction, the mixture being returned to the reactor beneath the surface of the reaction mixture. After addition of the fatty acid chloride, the reaction mixture is stirred for another 2 hours at 20–25° C. in the reactor and is then heated for about another 2 hours to 60–80° C. The reaction mixture is then left to cool to room temperature and adjusted to a pH of ca. 10 by addition of dilute hydrochloric acid.

The content of $C_{12}$–$C_{18}$ acyl glutamate disodium salt in the end product is 27.6%.

Example 3

Production of $C_{12}$–$C_{18}$ Acyl Glutamate Disodium Salt Without Removal of the Solvent 1,300 kg water, 10 kmol=1,870 kg monosodium glutamate (×1 $H_2O$), 160 kg diethylene glycol monoethyl ether and 1,100 kg 33% sodium hydroxide are introduced into a 15 $m^3$ reactor (FIG. 1) and stirred until a clear solution is obtained. The solution obtained is cooled to 10–20° C. The reactor and the circulation system are provided with a cooling jacket which dissipates the heat of reaction and guarantees a maximum temperature of 20–25° C. Before the start of the reaction, the pH is adjusted to ca. 12 with 11% sodium hydroxide. 7.7 kmol=1,825 kg cocoyl fatty acid chloride and 4,500 kg 11% NaOH are then simultaneously added (see plant concept) at such a rate that the reactor temperature does not exceed 20–25° C. and the pH stays between 11.5 and 12.5. Of the two reactants, the sodium hydroxide is preferably added to the reactor beneath the surface of the reaction mixture while the acid chloride is added from the holding vessel either to or before the mixer. A circulation pump circulates the reaction mixture throughout the reaction, the mixture being returned to the reactor beneath the surface of the reaction mixture. After addition of the fatty acid chloride, the reaction mixture is stirred for another 2 hours at 20–25° C. in the reactor and is then heated for about another 2 hours to 60–80° C. The reaction mixture is then left to cool to room temperature and adjusted to a pH of ca. 10 by addition of dilute hydrochloric acid.

The content of $C_{12}$–$C_{18}$ acyl glutamate disodium salt in the end product is 27.6%.

Example 4

Production of $C_{12}$–$C_{18}$ Acyl Glutamate Disodium Salt With Removal of the Solvent 1,300 kg water, 10 kmol=1,870 kg monosodium glutamate (×1 $H_2O$), 160 kg isopropanol and 1,100 kg 33% sodium hydroxide are introduced into a 15 $m^3$ reactor (FIG.

1) and stirred until a clear solution is obtained. The solution obtained is cooled to 10–20° C. The reactor and the circulation system are provided with a cooling jacket which dissipates the heat of reaction and guarantees a maximum temperature of 20–25° C. Before the start of the reaction, the pH is adjusted to ca. 12 with 11% sodium hydroxide. 7.7 kmol=1,825 kg cocoyl fatty acid chloride and 4,500 kg 11% NaOH are then simultaneously added (see plant concept) at such a rate that the reactor temperature does not exceed 20–25° C. and the pH stays between 11.5 and 12.5. Of the two reactants, the sodium hydroxide is preferably added to the reactor beneath the surface of the reaction mixture while the acid chloride is added from the holding vessel either to or before the mixer. A circulation pump circulates the reaction mixture throughout the reaction, the mixture being returned to the reactor beneath the surface of the reaction mixture. After addition of the fatty acid chloride, the reaction mixture is stirred for another 2 hours at 20–25° C. in the reactor and is then heated for about another 2 hours to 60–80° C.

If desired, the pressure is reduced to 300 to 400 mbar and a mixture of isopropanol/water is distilled off at 60 to 80° C. To avoid concentration of the reaction mixture and to make distillation more effective, steam is simultaneously introduced. Ca. 1,845 kg isopropanol/water distils off over a period of 1 hour, the isopropanol content decreasing by 1.5% to ca. 9 ppm. After cooling to room temperature, the solution is adjusted to a pH of ca. 10 with dilute hydrochloric acid and optionally adjusted to the desired final concentration by addition of water.

Example 5

540 kg 1,2-propylene glycol are also added to the produced in accordance with Example 2.

Comparison Example 1

Figure 2:
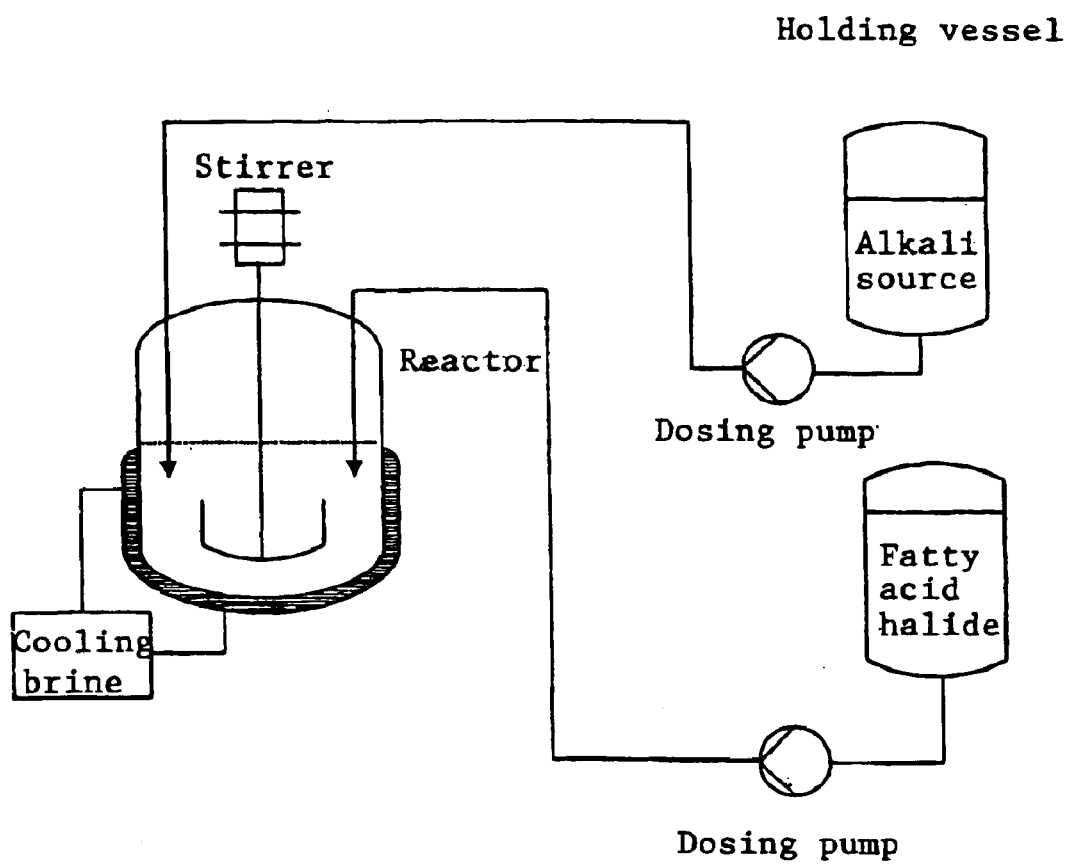
FIG. 2 is a process flow diagram for a process for the production of acylamino acids without a mixer.

Preparation of $C_{12}$–$C_{18}$ Acyl Glutamate Disodium Salt 2,279 kg water, 10 kmol=1,870 kg monosodium glutamate (×1 $H_2O$) and 1,870 kg 25% sodium hydroxide are introduced into a 15 m³ reactor (FIG. 2) and stirred until a clear solution is obtained. The solution obtained is cooled to 10–20° C. The reactor is provided with a cooling jacket which dissipates the heat of reaction and guarantees a maximum temperature of 20–25° C. Before the start of the reaction, the pH is adjusted to ca. 12 with 25% sodium hydroxide. 7.7 kmol=1,825 kg cocoyl fatty acid chloride and 1,540 kg 25% NaOH are then simultaneously added at such a rate that the reactor temperature does not exceed 20–25° C. and the pH stays between 11.5 and 12.5. The two reactants are preferably added to the reactor beneath the surface of the reaction mixture. The reaction mixture is intensively stirred with an Ikato Intermig stirrer at a rotational speed of 120 r.p.m. The experiment has to be terminated after addition of 208 kg acid chloride and 180 kg 25% sodium hydroxide because the foam has reached the rim of the cover of the 15 m³ reactor (net capacity: 6407 kg).

What is claim is:

1. A process for the production of acylamino acids comprising the steps of: (1) introducing a mixture comprised of at least one amino acid or amino acid salt and an alkali source into a reaction zone; (2) adding a mixture comprised of a fatty acid halide of the formula (I):

$$R^1COX \qquad (I)$$

wherein $R^1$ is an alkyl or alkenyl group having from 6 to 22 carbon atoms and X is chlorine, bromine or iodine to form a reaction mixture while continuously circulating the reaction mixture from the reaction zone through a mixing zone until all of the second mixture has been added to the reaction zone.

2. The process of claim 1 wherein the amino acid is glutamic acid, sarcosine, aspartic acid, alanine, valine, leucine, isoleucine, proline, hydroxyproline, glycine, serine, cysteine, cystine, threonine, histidine and salts thereof.

3. The process of claim 1 wherein the alkali source is comprised of an alkali metal hydroxide, an alkali metal carbonate, an amine or mixtures thereof.

4. The process of claim 1 wherein the mixing zone is a dynamic or a static mixer.

5. The process of claim 3 wherein the alkali source is dissolved in a solvent selected from the group consisting of acetone, methylethyl ketone, dioxane, tetrahydrofuran, methanol, ethanol, propanol, i-propanol, butanol, t-butanol, pentanol, isopentanol, trimethyl hexanol, glycerol, ethylene glycol, 2-methylpropane-1,3-diol, propylene glycol, dipropylene glycol, 1,3-butylene glycol, butane-1,2-diol, butane-1,4-diol, isopentyl diol, sorbitol, xylitol, mannitol, erythritol, pentaerythritol, ethanolamine, triethanolamine, 2-amino-2-methylpropanol, 1-amino-2-propanol, 1-amino-2-butanol, 1-methoxy-2-propanol, 2-methoxy ethanol, 2-ethoxy ethanol, 2-propoxy ethanol, 2-isopropoxy ethanol, 2-butoxy ethanol, 1-methoxy-2-propanol, 1-ethoxy-2-propanol, 1-propoxy-2-propanol, 1-isopropoxy-2-propanol, 1-butoxy-2-propanol, 1-isobutoxy-2-propanol, methoxy isopropanol, diethylene glycol monomethyl ether, diethylene glycol monomethyl ether, diethylene glycol monopropyl ether, diethylene glycol monoisopropyl ether, diethylene glycol monobutyl ether, triethylene glycol monomethyl ether, triethylene glycol monoethyl ether, triethylene glycol monopropyl ether, triethylene glycol monoisopropyl ether, triethylene glycol monobutyl ether, dipropylene glycol monomethyl ether, dipropylene glycol monoethyl ether, dipropylene glycol monopropyl ether, dipropylene glycol monoisopropyl ether, dipropylene glycol monobutyl ether, hexylene glycol, triacetin, propylene carbonate, and glycerol carbonate.

6. The process of claim 1 further comprising the step of adding a solvent selected from the group consisting of trimethyl hexanol, glycerol, 2-methylpropane-1,3-diol, propylene glycol, dipropylene glycol, 1,3-butylene glycol, butane-1,2-diol, butane-1,4-diol, isopentyl diol, sorbitol, xylitol, mannitol, erythritol, pentaerythritol, 1-methoxy-2-propanol, 2-methoxy ethanol, 2-ethoxy ethanol, 2-propoxy ethanol, 2-isopropoxy ethanol, 2-butoxy ethanol, 1-methoxy-2-propanol, 1-ethoxy-2-propanol, 1-propoxy-2-propanol, 1-isopropoxy-2-propanol, 1-butoxy-2-propanol, 1-isobutoxy-2-propanol, methoxy isopropanol, diethylene glycol monomethyl ether, diethylene glycol monoethyl ether, diethylene glycol monopropyl ether, diethylene glycol monoisopropyl ether, diethylene glycol monobutyl ether, triethylene glycol monomethyl ether, triethylene glycol monoethyl ether, triethylene glycol monopropyl ether, triethylene glycol monoisopropyl ether, triethylene glycol monobutyl ether, dipropylene glycol monomethyl ether, dipropylene glycol monoethyl ether, dipropylene glycol monopropyl ether, dipropylene glycol monoisopropyl ether, dipropylene glycol monobutyl ether, hexylene glycol and mixtures thereof.

7. A composition comprising:

(a) an acylamino acid, (b) from 3 to 10% by weight sodium chloride, (c) from 0.1 to 4% by weight free fatty acids, (d) from 1 to 11% by weight free amino acids, (e) from 0.1 to 6% by weight low molecular weight alcohol and (f) from 30 to 80% by weight water.